US012582618B2

(12) United States Patent
Marcus et al.

(10) Patent No.: US 12,582,618 B2
(45) Date of Patent: Mar. 24, 2026

(54) BIS-BIGUANIDE COMPOUNDS, PHARMACEUTICAL COMPOSITIONS AND USES IN MANAGING CANCER

(71) Applicant: Emory University, Atlanta, GA (US)

(72) Inventors: Adam Marcus, Atlanta, GA (US); Jessica Konen, Houston, TX (US); Rachel Commander, Atlanta, GA (US); Jamie Arnst, Atlanta, GA (US); Thota Ganesh, Alpharetta, GA (US)

(73) Assignee: Emory University, Atlanta, GA (US)

( * ) Notice: Subject to any disclaimer, the term of this patent is extended or adjusted under 35 U.S.C. 154(b) by 1135 days.

(21) Appl. No.: 17/434,606

(22) PCT Filed: Feb. 28, 2020

(86) PCT No.: PCT/US2020/020280
§ 371 (c)(1),
(2) Date: Aug. 27, 2021

(87) PCT Pub. No.: WO2020/176825
PCT Pub. Date: Sep. 3, 2020

(65) Prior Publication Data

US 2022/0168244 A1 Jun. 2, 2022

Related U.S. Application Data

(60) Provisional application No. 62/811,768, filed on Feb. 28, 2019.

(51) Int. Cl.

| | |
|---|---|
| ***A61K 31/155*** | (2006.01) |
| ***A61K 45/06*** | (2006.01) |
| ***A61P 35/00*** | (2006.01) |
| *C07C 279/26* | (2006.01) |

(52) U.S. Cl.
CPC ............ *A61K 31/155* (2013.01); *A61K 45/06* (2013.01)

(58) Field of Classification Search
CPC .. A61K 31/155; A61K 45/06; C07C 279/265; A61P 35/00
See application file for complete search history.

(56) References Cited

U.S. PATENT DOCUMENTS

| | | | | |
|---|---|---|---|---|
| 6,613,310 | B1 | 9/2003 | Campbell | |
| 7,470,428 | B2 | 12/2008 | Kuchroo | |
| 8,119,684 | B2 | 2/2012 | Yeh | |
| 2004/0077601 | A1 | 4/2004 | Adams | |
| 2005/0250709 | A1 | 11/2005 | Khodadoust | |
| 2019/0195858 | A1 | 6/2019 | Marcus | |
| 2021/0251934 | A1* | 8/2021 | Fliri | A61K 47/06 |

FOREIGN PATENT DOCUMENTS

| | | |
|---|---|---|
| CN | 107921283 | 4/2018 |
| WO | 2004004658 | 1/2004 |
| WO | 2005060951 | 7/2005 |

OTHER PUBLICATIONS

Tanzer JM, Slee AM, Kamay BA. Structural requirements of guanide, biguanide, and bisbiguanide agents for antiplaque activity. Antimicrob Agents Chemother. Dec. 1977;12(6):721-9. doi: 10.1128/AAC.12.6.721. PMID: 931371; PMCID: PMC430011. (Year: 1977).*
Fazio et al. Everolimus in advanced, progressive, well-differentiated, non-functional neuroendocrine tumors: RADIANT-4 lung subgroup analysis. Cancer Sci. Jan. 2018;109(1):174-181. doi: 10.1111/cas.13427. Epub Nov. 9, 2017. PMID: 29055056; PMCID: PMC5765303. (Year: 2017).*
Yang Z, Hackshaw A, Feng Q, Fu X, Zhang Y, Mao C, Tang J. Comparison of gefitinib, erlotinib and afatinib in non-small cell lung cancer: A meta-analysis. Int J Cancer. Jun. 15, 2017;140(12):2805-2819. doi: 10.1002/ijc.30691. Epub Mar. 27, 2017. PMID: 28295308 (Year: 2017).*
Cecil Textbook of Medicine, 20th Ed, vol. 1, 1997 (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
Shepard et al. Novel guanide-substituted compounds bind to CXCR4 and inhibit breast cancer metastasis Anti Cancer Drugs 2014, vol. 25, No. 1 (Year: 2014).*
Burell et al. The causes and consequences of genetic heterogeneity in cancer evolution, Nature, vol. 501, pp. 338-345 (2013).
Graber et al. Oral Disinfectants Inhibit Protein-Protein Interactions Mediated by the Anti-Apoptotic Protein Bcl-xL and Induce Apoptosis in Human Oral Tumor Cells, Angew Chem Int Ed Engl. 2013, 52(16):4487-91.
Hsu et al. Identification of approved and investigational drugs that inhibit hypoxia-inducible factor-1 signaling, Oncotarget, 2016, 7(7):8172-83.

(Continued)

*Primary Examiner* — Bruck Kifle
*Assistant Examiner* — Kevin S Martin
(74) *Attorney, Agent, or Firm* — Emory Patent Group

(57) ABSTRACT

This disclosure relates to methods of managing cancer using bis-biguanide compounds, such as alexidine, and pharmaceutical compositions comprising the same. In certain embodiments, this disclosure relates to methods of treating lung cancer comprising administering an effective amount of a bis-biguanide compound to a subject in need thereof. In certain embodiments, this disclosure relates to methods of treating small cell lung cancer comprising administering an effective amount of a bis-biguanide compound to a subject in need thereof. In certain embodiments, the subject is diagnosed with a lung cancer. In certain embodiments, the subject is diagnosed with small cell lung cancer. In certain embodiments, the subject is a human subject.

18 Claims, 7 Drawing Sheets

(56) References Cited

OTHER PUBLICATIONS

Konen et al. Image-guided genomics of phenotypically heterogeneous populations reveals vascular signalling during symbiotic collective cancer invasion, Nature Communications vol. 8, Article No. 15078 (2017).
Li et al. A Multicenter Double-blind Phase II Study of Metformin With Gefitinib as First-line Therapy of Locally Advanced NoneSmall-cell Lung Cancer, Clinical Lung Cancer, 2016, vol. 18, No. 3, 340-3.
Lo et al. Computational Cell Cycle Profiling of Cancer Cells for Prioritizating FDA-Approved Drugs wit Repurposing Potential, Scientific Reports, 2017, 7:11261, 1-12.
Mamouei et al. Alexidine dihydrochloride has broad spectrum activities against diverse fungal pathogens, bioRxiv, 2018, 429944, available at https://doi.org/10.1101/429944.
Niemi et al. Downregulation of the Mitochondrial Phosphatase PTPMT1 Is Sufficient to Promote Cancer Cell Death, PLoS ONE, 2013, 8(1): e53803.
Wei et al. Drug repositioning in head and neck squamous cell carcinoma: An integrated pathway analysis based on connectivity map and differential gene expression, Pathology—Research and Practice, 2019, vol. 215, Issue 6, 152378.
Yip et al. Potential use of alexidine dihydrochloride as an apoptosis-promoting anticancer agent, Mol Cancer Ther, 2006, 5(9):2234-40.
CN Office Action, Chinese Invention Patent Application No. 2020800166439, Aug. 31, 2023.
Extended European Search Report, EP Application 20763619.2, Jan. 2, 2023.
Tao et al. Discovery of a Potent and Selective BCL-XL Inhibitor with in Vivo Activity, ACS Med. Chem. Lett. 2014, 5, 1088-1093.

* cited by examiner

| | |
|---|---|
| Alexidine |  |
| AX-1 |  |
| AX-2 |  |
| AX-3 |  |
| AX-4 |  |

| | |
|---|---|
| AX5 |  |
| AX7 |  |
| AX10 |  |

TG-AX12

TG-AX13

Compound A

TG-AX15

TG-AX7

TG-AX14

BIS-BIGUANIDE COMPOUNDS, PHARMACEUTICAL COMPOSITIONS AND USES IN MANAGING CANCER

CROSS-REFERENCE TO RELATED APPLICATIONS

This application is the National Stage of International Application No. PCT/US2020/020280 filed Feb. 28, 2020, which claims the benefit of U.S. Provisional Application No. 62/811,768 filed Feb. 28, 2019. The entirety of each of these applications is hereby incorporated by reference for all purposes.

BACKGROUND

Non-small cell lung cancer is an umbrella term for several types of lung cancers that behave in a similar way such as squamous cell carcinoma, adenocarcinoma, and large cell carcinoma. Heavy smokers commonly develop small cell lung cancer (SCLC). The outcome for patients with SCLC remains unpredictable. While many SCLC patients respond to frontline chemotherapy, recurrence of disease is common. Recurrence following initial frontline therapy is associated with a higher risk of resistance to the available salvage treatment options. Thus, there is a need to identify improved therapies.

Konen et al. report an image-guided genomics technique termed spatiotemporal genomic and cellular analysis (SaGA) that allows for precise selection and amplification of living and rare cells. Nat Comm, 2017, 8:15078. SaGA was used on collectively invading 3D cancer cell packs to create purified leader and follower cell lines. The leader cell cultures are phenotypically stable and highly invasive in contrast to follower cultures that show phenotypic plasticity over time.

Yip et al. report the potential use of alexidine dihydrochloride as an apoptosis-promoting anticancer agent. Mol Cancer Ther, 2006, 5(9):2234-40. See also Graber et al. Oral disinfectants that inhibit protein-protein interactions mediated by the anti-apoptotic protein Bcl-xL and induce apoptosis in human oral tumor cells, Angew Chem Int Ed, 2013, 52:4487-4491; Niemi et al. Downregulation of the Mitochondrial Phosphatase PTPMT1 Is Sufficient to Promote Cancer Cell Death, PLoS ONE, 2013, 8(1):e53803; and Lo et al. Computational cell cycle profiling of cancer cells for prioritizing FDA-approved drugs with repurposing potential, Sci Rep, 2017, 7(1):11261.

References cited herein are not an admission of prior art.

SUMMARY

This disclosure relates to methods of managing cancer using bis-biguanide compounds, such as alexidine, and pharmaceutical compositions comprising the same. In certain embodiments, this disclosure relates to methods of treating lung cancer comprising administering an effective amount of a bis-biguanide compound to a subject in need thereof. In certain embodiments, this disclosure relates to methods of treating small cell lung cancer comprising administering an effective amount of a bis-biguanide compound to a subject in need thereof. In certain embodiments, the subject is diagnosed with a lung cancer. In certain embodiments, the subject is diagnosed with small cell lung cancer. In certain embodiments, the subject is a human subject.

This disclosure relates to bis-biguanide compounds and pharmaceutical composition comprising the same. In certain embodiments, the bis-biguanide compound is alexidine, derivative, or salt thereof. In certain embodiments, the bis-biguanide compound is chlorhexidine. In certain embodiments, the bis-biguanide or alexidine derivative has Formula I:

Formula I

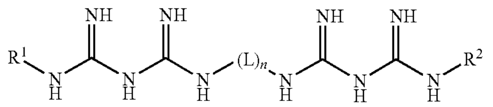

or salt thereof wherein, L is a linking group; n is 1 to 22; $R^1$ is an alkyl, aryl, or lipid, wherein $R^1$ is optionally substituted with one or more substituents, and $R^2$ is an alkyl, aryl, or lipid, wherein $R^2$ is optionally substituted with one or more substituents.

In certain embodiments, L is at each occurrence individually and independently selected from O, NH, C═O, $CH_2$, $OCH_2$, $CH_2O$, $NHCH_2$, $CH_2NH$, $OCH_2CH_2$, $CH_2CH_2O$, $NHCH_2CH_2$, or $CH_2CH_2NH$.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^1$ is a branched alkyl optionally substituted with one or more substituents and n is 2 to 8. In certain embodiments, $R^1$ is a branched alkyl optionally substituted with one or more substituents and n is 2 to 12. In certain embodiments, $R^1$ is a branched alkyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^2$ is a branched alkyl optionally substituted with one or more substituents and n is 2 to 8. In certain embodiments, $R^2$ is a branched alkyl optionally substituted with one or more substituents and n is 2 to 12. In certain embodiments, $R^2$ is a branched alkyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^1$ is a branched phenyl optionally substituted with one or more substituents and n is 2 to 8. In certain embodiments, $R^1$ is a branched phenyl optionally substituted with one or more substituents and n is 2 to 12. In certain embodiments, $R^1$ is a branched phenyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^2$ is a branched phenyl optionally substituted with one or more substituents and n is 2 to 8. In certain embodiments, $R^2$ is a branched phenyl optionally substituted with one or more substituents and n is 2 to 12. In certain embodiments, $R^2$ is a branched phenyl optionally substituted with one or more substituents and n is 2 to 22.

In certain embodiments, a bis-biguanide compound is administered in combination with a second chemotherapy agent. In certain embodiments, the subject is diagnosed with a lung cancer and the second chemotherapy agent is selected from bevacizumab, ramucirumab, crizotinib, erlotinib, gefitinib, afatinib dimaleate, ceritinib, ramucirumab, nivolumab, pembrolizumab, osimertinib, necitumumab, alectinib, atezolizumab, brigatinib, trametinib, dabrafenib, durvalumab, dacomitinib, lorlatinib, or combinations thereof.

In certain embodiments, the disclosure relates to uses of bis-biguanide compounds disclosed herein in the production of a medicament for the treatment or prevention of cancer as reported herein.

In certain embodiments, the disclosure relates to methods of preparing bis-biguanide compounds disclosed herein comprising mixing starting material and reagents disclosed herein under conditions that the compounds are formed.

BRIEF DESCRIPTION OF THE SEVERAL VIEWS OF THE DRAWING(S)

FIG. 1A illustrates certain bis-biguanide compounds of this disclosure. Alexidine has the chemical name 1,1'-(hexane-1,6-diyl)bis(5-(2-ethylhexyl)biguanidine). AX-1 has the chemical name 1-(2-ethylhexyl)-5-propylbiguanidine. AX-2 has the chemical name 1,1'-(hexane-1,6-diyl)bis(5-(methyl)biguanidine). AX-3 has the chemical name 1,1'-(butane-1,4-diyl)bis(5-(2-ethylhexyl)biguanidine). AX-4 has the chemical name 1,1'-(octane-1,8-diyl)bis(5-(2-ethylhexyl)biguanidine).

FIG. 1B illustrates certain bis-biguanide compounds of this disclosure. TG-AX5 has the chemical name 1,1'-(hexane-1,6-diyl)bis(5-(2-butylhexyl)biguanidine). TG-AX7 has the chemical name 1,1'-(hexane-1,6-diyl)bis(5-(2-ethylbutyl)biguanidine). TG-AX10 has the chemical name 1,1'-(hexane-1,6-diyl)bi(5-(4-methoxybutyl)biguanidine).

Figure 5:
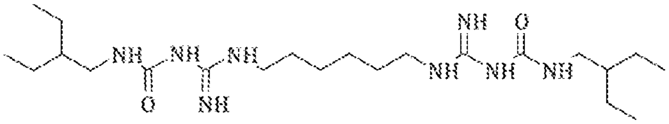
Figure 5:
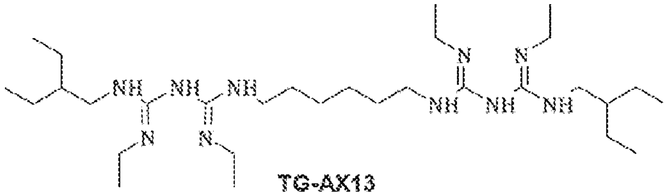
Figure 5:
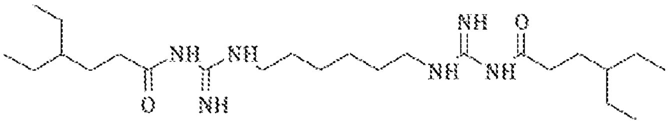
Figure 5:
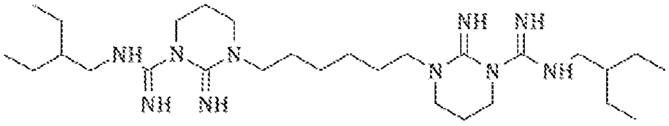
Figure 5:
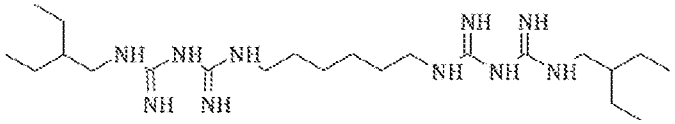
Figure 5:
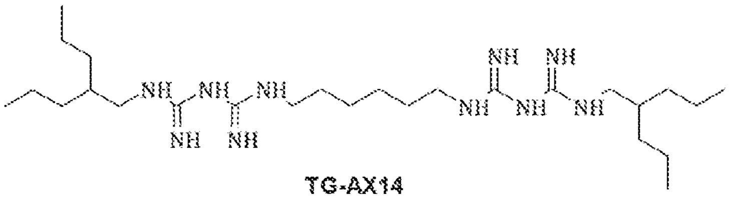

FIG. 5 illustrates certain bis-biguanide compounds and derivatives of this disclosure. Compound A has the chemical name 1,1'-(hexane-1,6-diyl)bis(guanyl)bis(3-(4-ethyl) hexanamide). TG-AX12 has the chemical name 1,1'-(hexane-1,6-diyl)bis(5-(2-ethylbutyl)guanylurea). TG-AX13 has the chemical name 1,1'-(hexane-1,6-diyl)bis(2-ethyl-4-ethyl-5-(2-ethylbutyl)biguanidine). TG-AX14 has the chemical name 1,1'-(hexane-1,6-diyl)bis(5-(2-propylpentyl)biguanidine). TG-AX15 has the chemical name 3,3'-(hexane-1,6-diyl)bis(N-(2-ethylbutyl)-2-iminotetrahydropyrimidine-1(2H)-carboximidamide).

DETAILED DISCUSSION

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the esophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, pheochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

A "chemotherapy agent," "chemotherapeutic," "anti-cancer agent" or the like, refer to molecules that are recognized to aid in the treatment of a cancer. Contemplated examples include the following molecules, prodrugs, or derivatives such In certain embodiments, an additional chemotherapy agent or combination is contemplated to be selected from abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed di sodium, copanli sib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof, such as a combination of cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); epirubicin, cisplatin, capecitabine (ECX); and methotrexate, vincristine, doxorubicin, cisplatin (MVAC).

As used herein, the terms "small cell lung cancer" refers to small cell carcinoma (oat cell cancer) or combined small cell carcinoma identified in lung tissue. Tests and procedures may be used to detect (find), diagnose, and stage small cell lung cancer. A subject may be diagnosed with small cell lung cancer by laboratory tests, sputum cytology, lung biopsy, e.g., fine-needle aspiration (FNA) biopsy of the lung, bronchoscopy, thoracoscopy, thoracentesis, mediastinoscopy, CT scan (CAT scan), or chest x-ray. Test samples of lung tissue or fluid, blood, urine, or other substances in the body may be used. These tests may be used to plan and check treatment or monitor the disease over time.

As used herein a "bis-biguanide compounds" refers to a compound with two bridging biguanidine groups, i.e., (—NH(C═NH)NH(C═NH)NH—), connected by a linking group. In certain embodiments, a bis-biguanide compound is alexidine [1,1'-(hexane-1,6-diyl)bis(5-(2-ethylhexyl)biguanidine)] and derivatives and chlorhexidine [1,1'-(hexane-1, 6-diyl)bis(3-(4-chlorophenyl)biguanidine)] and derivatives salts thereof, including the digluconate and the diacetate salts, especially the digluconate salts. Other salts include the dipropionate, the diformate, the dilactate, the dihydrochloride, the dihydrofluoride, the dihydrobromide, the sulfate, the phosphate, the succinate, the pivalate, the citrate, the tartrate and the maleate.

As used herein, the term "derivative" refers to a structurally similar compound that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group or hydrogen saturated carbon. The derivative may be a prodrug, comprise a lipid, polyethylene glycol, saccharide, polysaccharide. A derivative may be two or more compounds linked together by a linking group. It is contemplated that the linking group may be biodegradable. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than 0.63×10−4% w/w (at 25° C.) in water, which is the percent solubility of octane in water by weight. See Solvent Recovery Handbook, 2nd Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —C(OH)$R_m$, —C(OH)(OH)—, —C(OH)H, —C(Hal)$R_m$—, —C(Hal)(Hal)-, —C(Hal)H—, —C($N_3$)$R_m$—, —C(CN)$R_m$—, —C(CN)(CN)—, —C(CN)H—, —C($N_3$)($N_3$)—, —C($N_3$)H—, —O—, —S—, —N—, —NH—, —$NR_m$—, —(C═O)—, —(C═NH)—, —(C═S)—, —(C═$CH_2$)—, which may contain single, double, or triple bonds individually and independently between the R groups. If an R is branched with an $R_m$ it may be terminated with a group such as —$CH_3$, —H, —CH═$CH_2$, —CCH, —OH, —SH, —$NH_2$, —$N_3$, —CN, or—Hal, or two branched Rs may form a cyclic structure. It is contemplated that in certain instances, the total Rs or "m"

may be less than 100 or 50 or 25 or 10. Examples of linking groups include bridging alkyl groups and alkoxyalkyl groups.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR_aR_b$, $-NR_aC(=O)R_b$, $-NRaC(=O)NR_aNR_b$, $-NR_aC(=O)OR_b$, $-NR_aSO_2R_b$, $-C(=O)Ra$, $-C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isoxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl sub stituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

Bis-Biguanide or Alexidine Derivatives

In certain embodiments, the bis-biguanide compound is alexidine, derivative, or salt thereof. In certain embodiments, the bis-biguanide compound is chlorhexidine. In certain embodiments, the bis-biguanide or alexidine derivative has Formula I:

Formula I

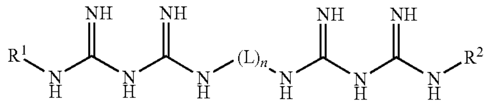

or salt thereof wherein, L is a linking group; n is 1 to 22; $R^1$ is an alkyl, aryl, or lipid, wherein $R^1$ is optionally substituted with one or more substituents, and $R^2$ is an alkyl, aryl, or lipid, wherein $R^2$ is optionally substituted with one or more substituents.

In certain embodiments, the bis-biguanide or alexidine derivative has Formula II:

Formula II

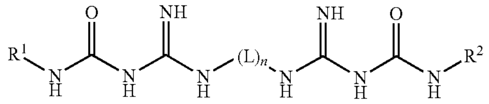

or salt thereof wherein, L is a linking group; n is 1 to 22; $R^1$ is an alkyl, aryl, or lipid, wherein $R^1$ is optionally substituted with one or more substituents, and $R^2$ is an alkyl, aryl, or lipid, wherein $R^2$ is optionally substituted with one or more substituents.

In certain embodiments, the bis-biguanide or alexidine derivative has Formula III:

Formula III

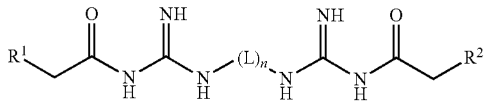

or salt thereof wherein, L is a linking group; n is 1 to 22; $R^1$ is an alkyl, aryl, or lipid, wherein $R^1$ is optionally substituted with one or more substituents, and $R^2$ is an alkyl, aryl, or lipid, wherein $R^2$ is optionally substituted with one or more substituents.

In certain embodiments, the bis-biguanide or alexidine derivative has Formula IV:

Formula IV

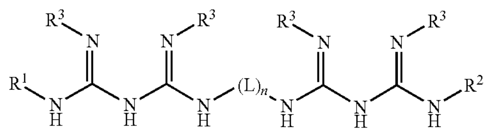

or salt thereof wherein, L is a linking group; n is 1 to 22; $R^1$ is an alkyl, aryl, or lipid, wherein $R^1$ is optionally substituted with one or more substituents, and $R^2$ is an alkyl, aryl, or lipid, wherein $R^2$ is optionally substituted with one or more substituents. $R^3$ is a hydrogen, alkyl, aryl, or lipid, wherein $R^3$ is optionally substituted with one or more substituents.

In certain embodiments, the bis-biguanide or alexidine derivative has Formula V:

Formula V

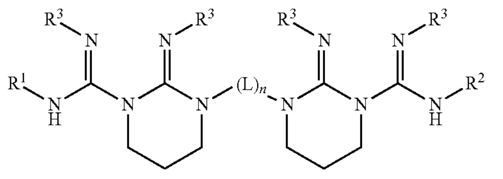

or salt thereof wherein, L is a linking group; n is 1 to 22; $R^1$ is an alkyl, aryl, or lipid, wherein $R^1$ is optionally substituted with one or more substituents, and $R^2$ is a hydrogen, alkyl, aryl, or lipid, wherein $R^2$ is optionally substituted with one or more substituents. $R^3$ is an alkyl, aryl, or lipid, wherein $R^3$ is optionally substituted with one or more substituents In certain embodiments, L is at each occurrence individually and independently selected from O, NH, C═O, $CH_2$, $OCH_2$, $CH_2O$, $NHCH_2$, $CH_2NH$, $OCH_2CH_2$, $CH_2CH_2O$, $NHCH_2CH_2$, or $CH_2CH_2NH$.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^1$ is a branched alkyl optionally substituted with one or more substituents and n is 2 to 8. In certain embodiments, $R^1$ is a branched alkyl optionally substituted with one or more substituents and n is 2 to 12. In certain embodiments, $R^1$ is a branched alkyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^2$ is a branched alkyl optionally substituted with one or more substituents and n is 2 to 8. In certain embodiments, $R^2$ is a branched alkyl optionally substituted with one or more substituents and n is 2 to 12. In certain embodiments, $R^2$ is a branched alkyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^1$ is a branched phenyl optionally substituted with one or more substituents and n is 2 to 8. In certain embodiments, $R^1$ is a branched phenyl optionally substituted with one or more substituents and n is 2 to 12. In certain embodiments, $R^1$ is a branched phenyl optionally substituted with one or more substituents and n is 2 to 22.

In certain embodiments, L is ($CH_2$) and n is 2 to 8. In certain embodiments, L is ($CH_2$) and n is 2 to 12. In certain embodiments, L is ($CH_2$) and n is 2 to 22. In certain embodiments, $R^2$ is a branched phenyl optionally substituted with one or more substituents and n is 2 to 8. In certain embodiments, $R^2$ is a branched phenyl optionally substituted with one or more substituents and n is 2 to 12. In certain embodiments, $R^2$ is a branched phenyl optionally substituted with one or more substituents and n is 2 to 22.

Methods of Use

In certain embodiments, this disclosure relates to methods of treating cancer or lung cancer comprising administering an effective amount of a bis-biguanide compound or derivative disclosed herein to a subject in need thereof. In certain embodiments, the subject is diagnosed with small cell lung cancer. In certain embodiments, this disclosure relates to methods of treating small cell lung cancer comprising administering an effective amount of a bis-biguanide compound to a subject in need thereof. In certain embodiments, the subject is diagnosed with a lung cancer. In certain embodiments, the subject is a human subject.

In certain embodiments, the disclosure relates to methods of treating or preventing cancer comprising administering a pharmaceutical composition disclosed herein to a subject diagnosed with, exhibiting symptoms of, or at risk of cancer. In certain embodiments, the cancer is selected from the group consisting of leukemia, melanoma, cervical, ovarian, colon, breast, gastric, lung, skin, ovarian, pancreatic, prostate, head, neck, and renal cancer. In certain embodiments, the pharmaceutical composition is administered in combination with a second chemotherapeutic agent.

In certain embodiments, the disclosure relates to therapeutic methods disclosed herein wherein the pharmaceutical compositions are administered before, after or during radiotherapy.

In certain embodiments, the subject is a human subject. In certain embodiments, this disclosure contemplates use as a first line treatment and use as a second line treatment, e.g., after growth of small cell lung cancer returns after a period of remission. In certain embodiments, the subject previously received a first chemotherapy treatment such as an administration schedule of etoposide, cisplatin, carboplatin, irinotecan, or combinations thereof.

In certain embodiments, this disclosure relates to methods of treating small cell lung cancer comprising administering an effective amount of a bis-biguanide compound in combination with cisplatin to a subject in need thereof.

In certain embodiments, this disclosure relates to methods of treating small cell lung cancer comprising administering an effective amount of a bis-biguanide compound in combination with etoposide to a subject in need thereof.

In certain embodiments, this disclosure relates to methods of treating small cell lung cancer comprising administering an effective amount of a bis-biguanide compound in combination with irinotecan to a subject in need thereof.

In certain embodiments, this disclosure relates to methods of treating small cell lung cancer comprising administering an effective amount of a bis-biguanide compound in combination with carboplatin, to a subject in need thereof.

In certain embodiments, this disclosure relates to methods of treating small cell lung cancer comprising administering an effective amount of a bis-biguanide compound in combination with cisplatin and etoposide to a subject in need thereof.

In certain embodiments, this disclosure relates to methods of treating small cell lung cancer comprising administering an effective amount of a bis-biguanide compound in combination with carboplatin and etoposide to a subject in need thereof.

In certain embodiments, this disclosure relates to methods of treating small cell lung cancer comprising administering an effective amount of a bis-biguanide compound in combination with carboplatin and irinotecan to a subject in need thereof.

In certain embodiments, this disclosure relates to methods of treating small cell lung cancer comprising administering an effective amount of alexidine, derivative or salt in combination with cisplatin to a subject in need thereof.

In certain embodiments, this disclosure relates to methods of treating small cell lung cancer comprising administering an effective amount of alexidine, derivative or salt in combination with etoposide to a subject in need thereof.

In certain embodiments, this disclosure relates to methods of treating small cell lung cancer comprising administering an effective amount of alexidine, derivative or salt in combination with irinotecan to a subject in need thereof.

In certain embodiments, this disclosure relates to methods of treating small cell lung cancer comprising administering an effective amount of alexidine, derivative or salt in combination with carboplatin, to a subject in need thereof.

In certain embodiments, this disclosure relates to methods of treating small cell lung cancer comprising administering an effective amount of alexidine, derivative or salt in combination with cisplatin and etoposide to a subject in need thereof.

In certain embodiments, this disclosure relates to methods of treating small cell lung cancer comprising administering an effective amount of alexidine, derivative or salt thereof in combination with carboplatin and etoposide to a subject in need thereof.

In certain embodiments, this disclosure relates to methods of treating small cell lung cancer comprising administering an effective amount alexidine, derivative or salt in combination with carboplatin and irinotecan to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with cisplatin to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with etoposide to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with irinotecan to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with carboplatin, to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with cisplatin and etoposide to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with carboplatin and etoposide to a subject in need thereof.

In certain embodiments, this disclosure relates to methods of treating small cell lung cancer comprising administering an effective amount of AX-3 [1,1'-(butane-1,4-diyl)bis(5-(2-ethylhexyl)biguanidine)] or salt in combination with carboplatin and irinotecan to a subject in need thereof.

In certain embodiments, this disclosure relates to methods of treating small cell lung cancer comprising administering an effective amount of AX-4 [1,1'-(octane-1,8-diyl)bis(5-(2-ethylhexyl)biguanidine)] or salt in combination with cisplatin to a subject in need thereof.

In certain embodiments, this disclosure relates to methods of treating small cell lung cancer comprising administering an effective amount of AX-4 [1,1'-(octane-1,8-diyl)bis(5-(2-ethylhexyl)biguanidine)] or salt in combination with etoposide to a subject in need thereof.

In certain embodiments, this disclosure relates to methods of treating small cell lung cancer comprising administering an effective amount of AX-4 [1,1'-(octane-1,8-diyl)bis(5-(2-ethylhexyl)biguanidine)] or salt in combination with irinotecan to a subject in need thereof.

In certain embodiments, this disclosure relates to methods of treating small cell lung cancer comprising administering an effective amount of AX-4 [1,1'-(octane-1,8-diyl)bis(5-(2-ethylhexyl)biguanidine)] or salt in combination with carboplatin, to a subject in need thereof.

In certain embodiments, this disclosure relates to methods of treating small cell lung cancer comprising administering an effective amount of AX-4 [1,1'-(octane-1,8-diyl)bis(5-(2-ethylhexyl)biguanidine)] or salt in combination with cisplatin and etoposide to a subject in need thereof.

In certain embodiments, this disclosure relates to methods of treating small cell lung cancer comprising administering an effective amount of AX-4 [1,1'-(octane-1,8-diyl)bis(5-(2-ethylhexyl)biguanidine)] or salt in combination with carboplatin and etoposide to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with cisplatin to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with etoposide to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with irinotecan to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with carboplatin, to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with cisplatin and etoposide to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with carboplatin and etoposide to a subject in need thereof.

In certain embodiments, this disclosure relates to methods of treating small cell lung cancer comprising administering an effective amount of AX-7 [1,1'-(hexane-1,6-diyl)bis(5-(2-ethylbutyl)biguanidine)] or salt in combination with carboplatin and irinotecan to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with cisplatin to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with etoposide to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with irinotecan to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with carboplatin, to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with cisplatin and etoposide to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with carboplatin and etoposide to a subject in need thereof.

In certain embodiments, this disclosure relates to methods of treating small cell lung cancer comprising administering an effective amount of Compound A having the chemical name 1,1'-(hexane-1,6-diyl)bis(guanyl)bis(3-(4-ethyl) hexanamide) or salt in combination with carboplatin and irinotecan to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with cisplatin to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with etoposide to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with irinotecan to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with carboplatin, to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with cisplatin and etoposide to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with carboplatin and etoposide to a subject in need thereof.

In certain embodiments, this disclosure relates to methods of treating small cell lung cancer comprising administering an effective amount of TG-AX12 having the chemical name 1,1'-(hexane-1,6-diyl)bis(5-(2-ethylbutyl)guanylurea) or salt in combination with carboplatin and irinotecan to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl) biguanidine) or salt in combination with cisplatin to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl) biguanidine) or salt in combination with etoposide to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl) biguanidine) or salt in combination with irinotecan to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl) biguanidine) or salt in combination with carboplatin, to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl) biguanidine) or salt in combination with cisplatin and etoposide to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl) biguanidine) or salt in combination with carboplatin and etoposide to a subject in need thereof.

In certain embodiments, this disclosure relates to methods of treating small cell lung cancer comprising administering an effective amount of TG-AX13 having the chemical name 1,1'-(hexane-1,6-diyl)bis(2-ethyl-4-ethyl-5-(2-ethylbutyl)

biguanidine) or salt in combination with carboplatin and irinotecan to a subject in need thereof.

In certain embodiments, this disclosure relates to methods of treating small cell lung cancer comprising administering an effective amount of TG-AX14 having the chemical name 1,1'-(hexane-1,6-diyl)bis(5-(2-propylpentyl)biguanidine) or salt in combination with etoposide to a subject in need thereof.

In certain embodiments, this disclosure relates to methods of treating small cell lung cancer comprising administering an effective amount of TG-AX14 having the chemical name 1,1'-(hexane-1,6-diyl)bis(5-(2-propylpentyl)biguanidine) or salt in combination with irinotecan to a subject in need thereof.

In certain embodiments, this disclosure relates to methods of treating small cell lung cancer comprising administering an effective amount of TG-AX14 having the chemical name 1,1'-(hexane-1,6-diyl)bis(5-(2-propylpentyl)biguanidine) or salt in combination with carboplatin, to a subject in need thereof.

In certain embodiments, this disclosure relates to methods of treating small cell lung cancer comprising administering an effective amount of TG-AX14 having the chemical name 1,1'-(hexane-1,6-diyl)bis(5-(2-propylpentyl)biguanidine) or salt in combination with cisplatin and etoposide to a subject in need thereof.

In certain embodiments, this disclosure relates to methods of treating small cell lung cancer comprising administering an effective amount of TG-AX14 having the chemical name 1,1'-(hexane-1,6-diyl)bis(5-(2-propylpentyl)biguanidine) or salt in combination with carboplatin and etoposide to a subject in need thereof.

In certain embodiments, this disclosure relates to methods of treating small cell lung cancer comprising administering an effective amount of TG-AX14 having the chemical name 1,1'-(hexane-1,6-diyl)bis(5-(2-propylpentyl)biguanidine) or salt in combination with carboplatin and irinotecan to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with cisplatin to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with etoposide to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with irinotecan to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with carboplatin, to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with cisplatin and etoposide to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with carboplatin and etoposide to a subject in need thereof.

In certain embodiments, this disclosure relates to methods of treating small cell lung cancer comprising administering an effective amount of TG-AX15 having the chemical name 3,3'-(hexane-1,6-diyl)bis(N-(2-ethylbutyl)-2-iminotetrahydropyrimidine-1(2H)-carboximidamide) or salt in combination with carboplatin and irinotecan to a subject in need thereof.

In certain embodiments, methods contemplate administration in cycles with a period of treatment of daily for 1 to 3 days followed by a rest period of at least one, two, three or more days. In certain embodiments, the cycle generally lasts about 2 to 4 weeks, and/or for 2 to 6 cycles, 2 to 7 cycles, or 2 to 8 cycles.

In certain embodiments, this disclosure contemplates methods wherein if during initial treatment cancer progresses during treatment or returns after treatment with etoposide, cisplatin, irinotecan, or combinations thereof, then the subject is administered a cycle of bis-biguanide compounds disclosed herein optionally in combination with other chemotherapy agents.

Pharmaceutical Compositions

In certain embodiment, this disclosure contemplates pharmaceutical compositions comprising bis-biguanide compounds disclosed herein and pharmaceutically acceptable excipient. In certain embodiments, this disclosure contemplates the production of a medicament comprising compounds disclosed herein and uses for methods disclosed herein.

Pharmaceutical compositions typically comprise an effective amount of a compound and a suitable pharmaceutical acceptable carrier. The preparations can be prepared in a manner known per se, which usually involves mixing the compounds according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

In certain embodiments, the disclosure relates to pharmaceutical compositions comprising compounds disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide. Optionally, the pharmaceutical composition further comprises a second clotting agent such as aminocaproic acid (ε-aminocaproic acid), tranexamic acid, fibrinogen, and vitamin K.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the compounds may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

In certain embodiments, production processes are contemplated which two components, bis-biguanide compounds disclosed herein and a pharmaceutical carrier, are provided already in a combined dry form ready to be reconstituted together. In other embodiments, it is contemplated that bis-biguanide compounds disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated compounds can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as syringes, vials, tubes, etc. The pharmaceutical composition may then preferably be applied via specific needles of the syringe or via suitable catheters. A typical diluent comprises water for injection, and NaCl (preferably 50 to 150 mM, especially 110 mM), $CaCl_2$ (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

In certain embodiments, this disclosure contemplates a kit comprising a pharmaceutical composition disclosed herein and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

EXAMPLES

Identification of Alexidine hydrochloride

Figure 1A:
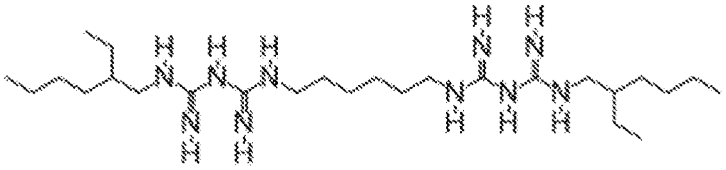
Figure 1A:
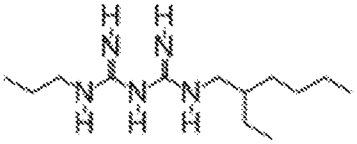
Figure 1A:
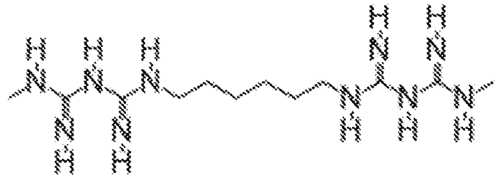
Figure 1A:
Figure 1A:
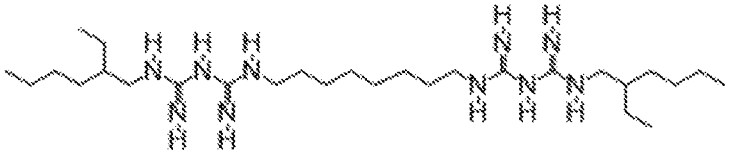
Figure 1B:
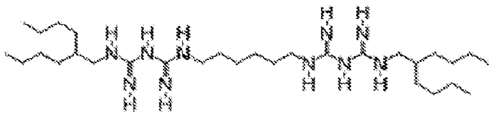
Figure 1B:
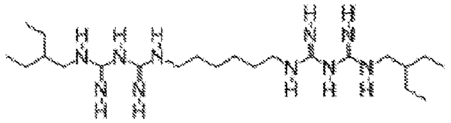
Figure 1B:
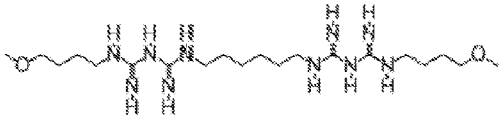
Figure 2A:
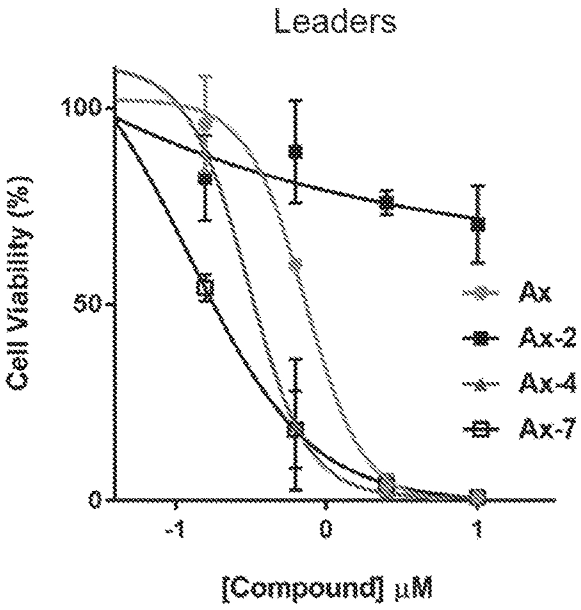
FIG. 2A shows data on dose-dependent viability of H1299 (human lung cells derived from metastatic lymph node) leader cells isolated by spatiotemporal genomic and cellular analysis (SaGA), after 72 h treatment with Alexidine and analogs AX-2, AX-4, and AX-7.
Figure 2B:
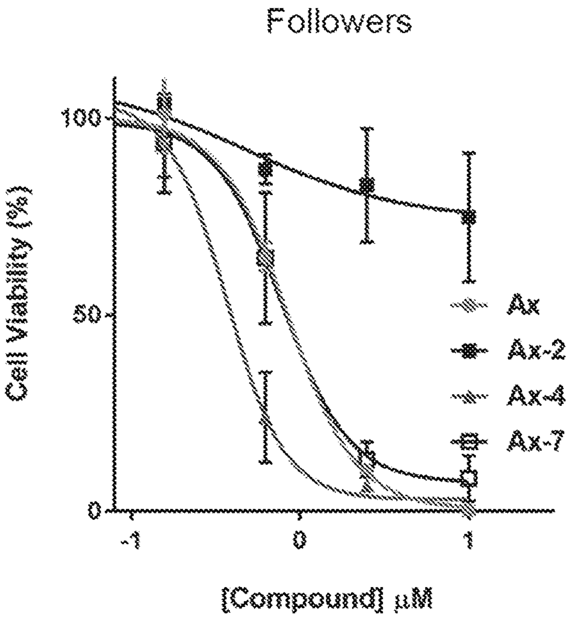
FIG. 2B shows data for follower cells isolated by SaGA.
Figure 2C:
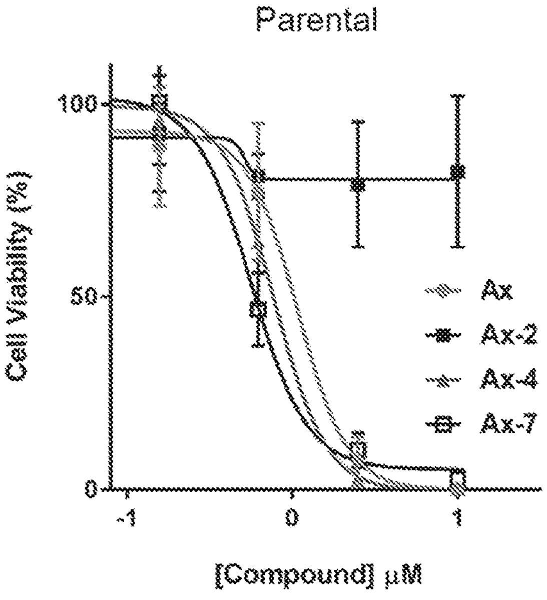
FIG. 2C shows data for parental cells isolated by SaGA.
Figure 3:
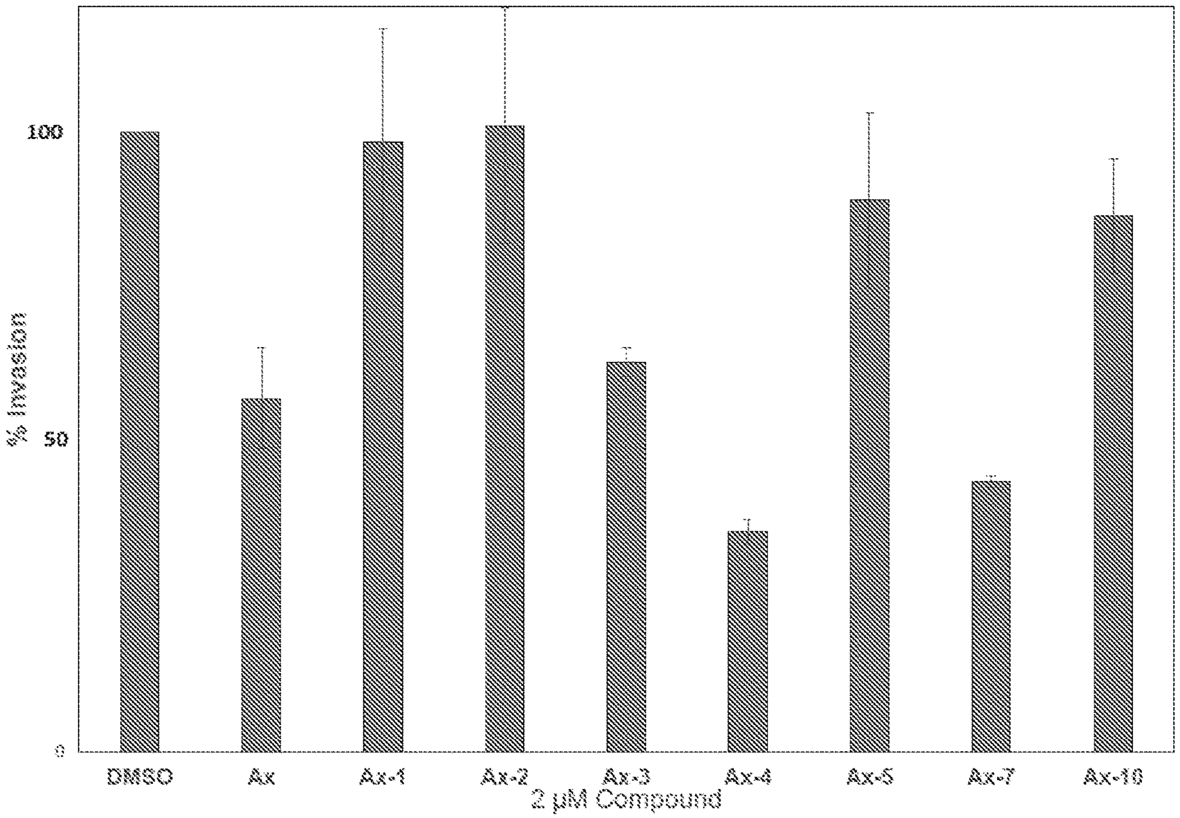
FIG. 3 shows on the inhibition of 3D invasion of H1299 leaders into Matrigel at 48 h.
Figure 4A:
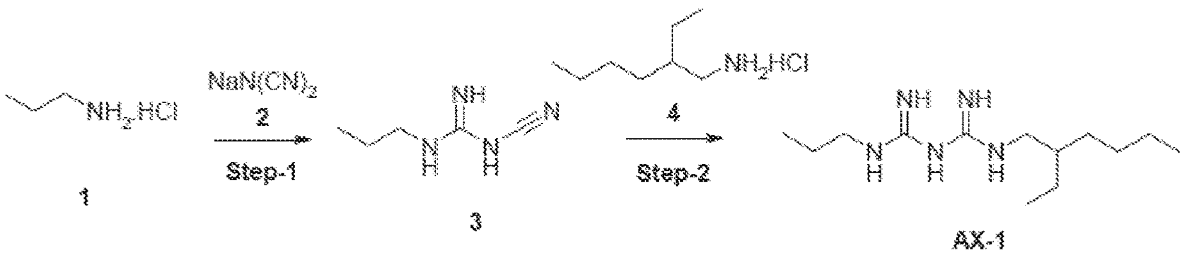
FIG. 4A illustrates methods of making embodiments of this disclosure.
Figure 4B:
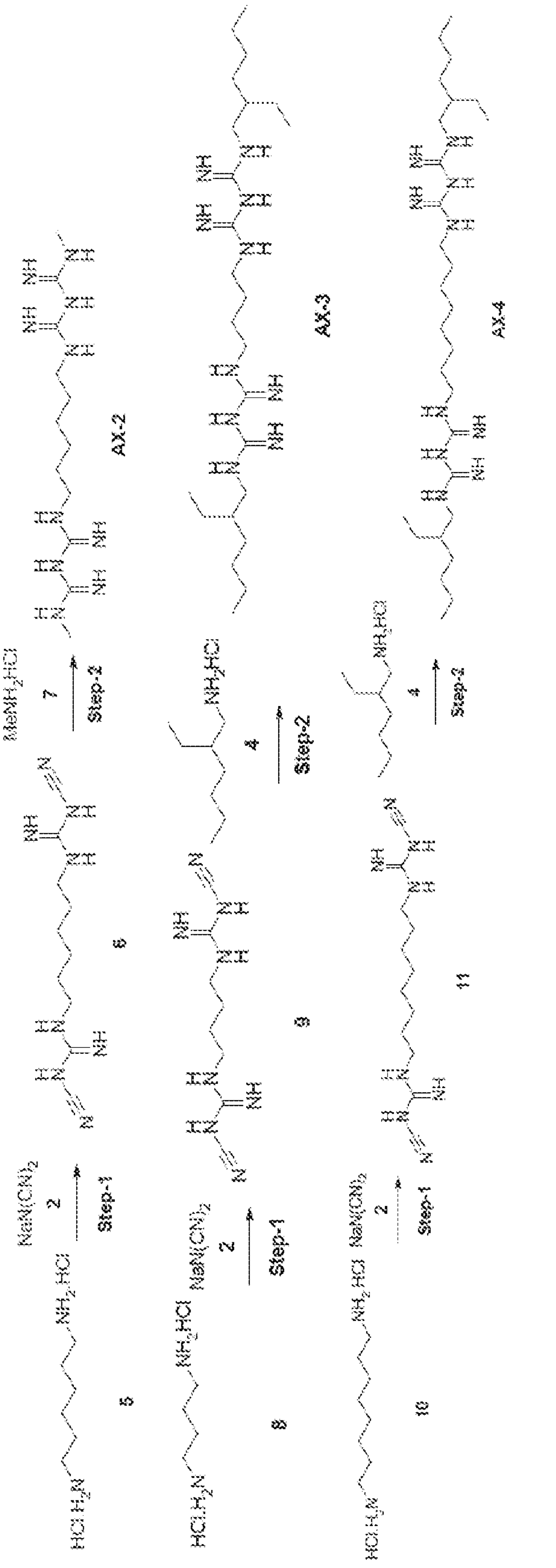
FIG. 4B illustrates methods of making embodiments of this disclosure.
Figure 4C:
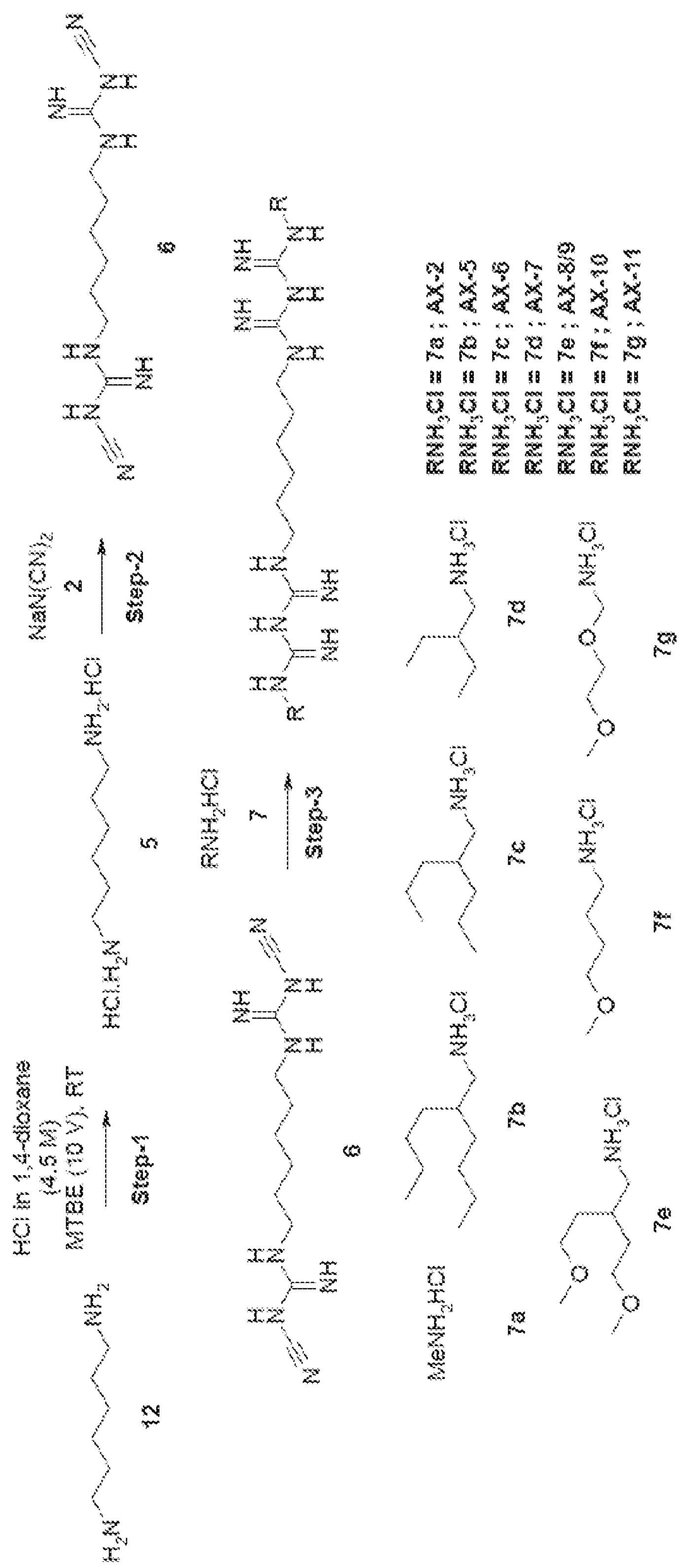
FIG. 4C illustrates methods of making embodiments of this disclosure.

Scientific data indicates that rare and phenotypically heterogeneous cancer cells, hidden within the larger population of patient tumor cells, serve as a major cause of patient relapse and poor clinical outcome. See e.g., Burrell et al., Nature, 2013, 501:338-345. Spatiotemporal genomic and cellular analysis (SaGA) is a technique which involves a combination of microscopy and genomics to isolate rare cells. See Konen et al. Nat Comm, 2017, 8:15078. Dendra2 is a photoconvertible fluorophore which emits green fluorescence. However, when excited by 405 nm light, green fluorescence is converted to red fluorescence due to cleavage of a histidine. Therefore, with single cell precision, any cancer cell expressing Dendra2 can be optically highlighted (turned red) using a point scanning confocal microscope. A region of interest is drawn around the cell(s) of interest, based upon by transmitted light or fluorescent protein tags. This region can be exposed to a 405 nm laser, resulting in near instantaneous photoconversion of Dendra2, and photomarking the cell red. Single cells can be photoconverted, without inducing any measurable photoconversion of neighboring cells. Cells are extracted from the 3-D environment using dispase for 15 minutes (collagenase for collagen). Cells are then sorted to separate red photoconverted cells from green cells using a FACS. Isolated cells are grown in culture using standard cell culture techniques. Spatiotemporal genomic and cellular analysis (SaGA) was used to identify rare lung cancer cells which were then subject to drug screening. The compound alexidine (FIG. 1A) was identified to disrupt metastasis by targeting a rare cell type within the invasive cell pack (i.e., the leader cell subpopulation). See FIG. 2A.

What is claimed is:

1. A method of treating lung cancer comprising administering 1,1'-(octane-1,8-diyl)bis(5-(2-ethylhexyl)biguanidine) or salt thereof to a subject in need thereof.

2. The method of claim 1 wherein 1,1'-(octane-1,8-diyl)bis(5-(2-ethylhexyl)biguanidine) or salt thereof is administered in combination with a second chemotherapy agent, wherein the second chemotherapy agent is selected from bevacizumab, ramucirumab, crizotinib, erlotinib, gefitinib, afatinib dimaleate, ceritinib, ramucirumab, nivolumab, pembrolizumab, osimertinib, necitumumab, alectinib, atezolizumab, brigatinib, trametinib, dabrafenib, durvalumab, dacomitinib, lorlatinib, or combinations thereof.

3. The method of claim 1, wherein the subject is a human.

4. A pharmaceutical composition comprising a compound 1,1'-(octane-1,8-diyl)bis(5-(2-ethylhexyl)biguanidine) or salt thereof and a pharmaceutically acceptable excipient.

5. The pharmaceutical composition of claim 4, wherein the composition is an aqueous pH buffered solution between 6 and 8.

6. The pharmaceutical composition of claim 4 in the form of a capsule, tablet, pill, powder, or granule.

7. The pharmaceutical composition of claim 4, wherein the pharmaceutically acceptable excipient is selected from a filler, glidant, binder, disintegrant, lubricant, or saccharide.

8. The pharmaceutical composition of claim 4, further comprising ethanol, propylene glycol, polyethylene glycol, or glycerol.

9. The pharmaceutical composition of claim 4, further comprising an antibacterial or antifungal agent.

10. The pharmaceutical composition of claim 4, further comprising aluminum monostearate or gelatin.

11. The pharmaceutical composition of claim 4, further comprising sodium citrate or dicalcium phosphate.

12. The pharmaceutical composition of claim 4, further comprising starch, lactose, sucrose, glucose, mannitol or silicic acid.

13. The pharmaceutical composition of claim 4, further comprising carboxymethylcellulose, alginate, gelatin, or polyvinylpyrrolidone.

14. The pharmaceutical composition of claim 4, further comprising calcium carbonate, starch, alginic acid, or sodium carbonate.

15. The pharmaceutical composition of claim 4, further comprising cetyl alcohol or glycerol monostearate.

16. The pharmaceutical composition of claim 4, further comprising kaolin or bentonite.

17. The pharmaceutical composition of claim 4, further comprising calcium stearate, magnesium stearate, or sodium lauryl sulfate.

18. The pharmaceutical composition of claim 4, further comprising isopropyl alcohol, ethyl carbonate, ethyl acetate, benzyl alcohol, benzyl benzoate, or dimethylformamide.

* * * * *